United States Patent

Chen et al.

[11] Patent Number: 5,925,604
[45] Date of Patent: Jul. 20, 1999

[54] MILD COLD PEARLIZING CONCENTRATES

[75] Inventors: Pu Chen, Singapore, Singapore; Joseph Niu, Houston, Tex.; Siew Fang Yoong, Singapore, Singapore

[73] Assignee: Rhodia Inc., Cranbury, N.J.

[21] Appl. No.: 08/677,258

[22] Filed: Jul. 9, 1996

Related U.S. Application Data

[63] Continuation of application No. 08/367,381, Dec. 30, 1994, Pat. No. 5,560,873.

[51] Int. Cl.⁶ .............................. C11D 1/72; C11D 1/83; C11D 1/94
[52] U.S. Cl. .................. 510/124; 510/120; 510/123; 510/125; 510/128; 510/137; 510/138; 510/158; 510/159; 510/416
[58] Field of Search ................... 510/120, 124, 510/125, 123, 128, 137, 138, 158, 159, 416

[56] References Cited

U.S. PATENT DOCUMENTS

| | | | |
|---|---|---|---|
| 4,486,334 | 12/1984 | Horiuchi et al. | 252/312 |
| 4,534,877 | 8/1985 | Russell et al. | 252/106 |
| 4,728,457 | 3/1988 | Fieler et al. | 252/174.15 |
| 4,824,594 | 4/1989 | Hoeffkes et al. | 252/174.21 |
| 4,948,528 | 8/1990 | Hoeffkes et al. | 252/357 |
| 5,017,305 | 5/1991 | Hoeffkes et al. | 252/311 |
| 5,151,209 | 9/1992 | Mc Call et al. | 252/174.15 |
| 5,152,914 | 10/1992 | Forster et al. | 252/174 |
| 5,198,209 | 3/1993 | Zhou et al. | 424/71 |
| 5,246,695 | 9/1993 | Hintz et al. | 424/70 |
| 5,252,325 | 10/1993 | Bires et al. | 424/71 |
| 5,275,755 | 1/1994 | Sebag et al. | 252/174.15 |
| 5,409,640 | 4/1995 | Giret et al. | 252/596 |
| 5,409,705 | 4/1995 | Kita et al. | 424/401 |

FOREIGN PATENT DOCUMENTS

| | | |
|---|---|---|
| 416447 | 3/1991 | European Pat. Off. . |
| 485212 | 5/1992 | European Pat. Off. . |
| 573341 | 12/1993 | European Pat. Off. . |
| 6293630 | 10/1994 | Japan . |

*Primary Examiner*—Mark Kopec
*Assistant Examiner*—Gregory R. Delcotto
*Attorney, Agent, or Firm*—John A. Shedden; Craig M. Bell

[57] ABSTRACT

Novel ultra-mild cold pearlizing concentrates provide pearlescent personal hair and skin compositions such as shampoos and beauty soaps with added luster and sheen.

9 Claims, No Drawings

MILD COLD PEARLIZING CONCENTRATES

This application is a continuation of 08/367,381 filed Dec. 30, 1994, now U.S. Pat. No. 5,560,873.

FIELD OF INVENTION

The present invention relates generally to hair and skin compositions such as soaps and shampoos for washing the skin and conditioning the hair. More particularly, the present invention relates to ultra-mild cold pearlescent concentrates used in said soaps and shampoos which impart an iridescent sheen or glow to these compositions.

BACKGROUND OF THE INVENTION

Hair conditioning shampoos and cosmetic soaps are well known in the art and have been described extensively in both the patent and non-patent journal literature. Cationic surfactants such as quaternary ammonium salts and anionic surfactants such as fatty alcohol sulfates and alkyl benzene sulfonates have been employed in hair rinses, soaps and shampoos as conditioning agents together with other water insoluble conditioning compounds such as silicones, waxes, grease and oils. Shampoos and soaps have always been produced in a variety of different forms such as solid bars, gels, creams and liquids.

Pearlescent shampoos are comprised of a number of ingredients such as stabilizing agents, pearlescent agents, conditioners, emulsifiers and hydrating agents. Pearlescent agents produce a shiny glow-like look to the compositions by the incorporation of substances which, after cooling, precipitate in the form of fine crystals resembling mother of pearl and which remain dispersed in the preparation. Known pearlizing agents include the mono- and diesters of glycol and glycerol with $C_{16}$–$C_{22}$ fatty acids. However, most pearlescent agents of the prior art, if used by themselves, have to be heated above their melting points for incorporation into a final formulation. The heating step and the conditions after the heating, e.g., the mixing, storage and/or cooling stages are difficult to control and thus the pearlescence condition is ofttimes not optimized, i.e., less than ideal.

"Cold pearlescent concentrates" i.e., those that can be subsequently formulated at room temperature, are known to offer a more consistent final pearlescent product.

The room temperature blending not only saves energy, but also eliminates many inconsistencies that occur with high temperature mixing.

Cocodiethanolamide has been used to prepare these cold pearlescent concentrates since it is liquid at room temperature and thus does not require a melting step to prepare the formulations; however, studies have raised concern that the diethanolamine, often present as a by-product of the cocodiethanolamide production, may form potentially carcinogenic nitrosamines. Thus, the use of cocodiethanolamide in pearlescent personal hair care and skin products such as cosmetics, facial soaps and shampoos has been questioned from a health standpoint.

Furthermore, alkyl sulfates and ethoxylated alkyl sulfates such as sodium laureth (3EO) sulfate, which also can be used in cold pearlescent concentrates, have been found to cause skin irritation.

It would certainly be advantageous then, to have a safe pearlescent agent for use in shampoo, lipstick and personal skin care products without the presence of 1) the cocodiethanolamide as a component of the formulation if the health concerns have any basis whatsoever and 2) the irritation producing alkyl sulfates and ethoxylated alkyl sulfates.

U.S. Pat. Nos. 5,290,480 and 5,290,482 to Marschner et. al. disclose surfactant compositions comprising betaine/ cocoamide complexes for use in shampoo and skin cleansing products. The complexes are combined with a cationic, nonionic, amphoteric or anionic surfactant to provide improved lather and conditioning characteristics. Cocodiethanolamide is widely used in these shampoo compositions. See U.S. Pat. No. 4,535,877 to Russell et. al. Cocoamidopropyl betaine is also a common shampoo ingredient often used as a conditioner or foam enhancer to increase the richness of the lather. See U.S. Pat. No. 4,490,355 to Desai.

U.S. Pat. No. 5,217,711 to DeOliveira et. al. disclose a hair treatment system consisting of a shampoo comprising, among other things, a pearlizing agent consisting of glycol distearate and a cocodiethanolamide. U.S. Pat. No. 5,019,376 to Vick teaches pearlescent "crystals" in a shampoo formulation formed by the reaction between a fatty acid and a fatty monoalcohol. U.S. Pat. No. 4,959,206 to Noguera et. al. teaches distearate of ethylene glycol and laurylsulfosuccinate as pearlescent agents but again, cocodiethanolamide is a necessary pearlescent stabilizer.

U.S. Pat. No. 4,938,953 to Pena discloses conditioning shampoos comprised of a fatty acid sulfate or a fatty alcohol ether sulfate, cocoamidopropyl betaine and cocoamidodiethanolamine. This composition also utilizes sodium lauryl sulfate as a stabilizing agent. U.S. Pat. No. 5,271,930 to Walele et. al. discloses the use of novel benzoic acid esters of polyalkoxylated block co-polymers as pearlescent agents in hair and skin care compositions.

Pearlizing agents conventionally can contain ethylene glycol monostearate, ethylene glycol distearate, guanine bismuth oxychloride on mica and mixtures thereof. U.S. Pat. No. 4,654,207 to Preston teaches a pearlescent shampoo wherein the pearlescing agent is a fatty acid ester, such as myristyl myristate or cetyl myristate, which is added to the shampoo base from a substantially anhydrous solubilizing agent such as a surfactant. A number of other prior art patents such as U.S. Pat. No. 4,608,392 to Jaquet et. al. describe the use of fatty alcohols and fatty acid quaternary ammonium compounds in the pearlescent blends. U.S. Pat. No. 5,019,376 to Vick et. al. also teaches the use of a quaternary ammonium compounds such as stearyl dimethyl benzyl ammonium chloride together with a $C_{12}$–$C_{16}$ fatty acid and cetyl alcohol.

U.S. Pat. No. 5,213,792 to Grundemen discloses hair conditioning compositions containing a pearlescent agent comprised of glycerin, a monolauric acid ester, a $C_{10}$–$C_{18}$ fatty alcohol, a quaternary ammonium compound, water and any one of a number of dyes, antioxidants and the like. All of these compositions also use cocodiethanolamide in one form or another for pearlescence or some other related function.

U.S. Pat. No. 4,777,038 to Scheuffgen discloses a free flowing pearlescent concentrate which allegedly remains stable without the sedimentation of the pearlescent crystals during storage. The composition is comprised of at least one mono- and diester of ethylene glycol or propylene glycol, a fatty acid monoethanolamine, ethylene glycol distearate, coconut oil and fatty alcohol. The sheen is provided by the appearance of fine, pearlescent crystals. U.S. Pat. Nos. 4,824,594, 4,948,528 and 5,017,305 to Hoeffkes et. al. all disclose and claim variations of a free flowing pearlescent concentrate comprising a $C_{12}$–$C_{18}$ coconut oil fatty acid monoethanolamide, a $C_{16}$–$C_{22}$ fatty alkyl ester, and at least one ethylene or propylene glycol ester or diester. These pearlescent agents act as emulsifiers which provide free flowing dispersions that allegedly combine high brilliance and stability with other cationic surfactant components.

U.S. Pat. No. 5,198,209 to Zhou et. al. discloses a conditioning shampoo comprising a mixture of anionic, cationic and nonionic surfactants and suggests the use of ethylene glycol stearate among others as a pearlescent agent.

U.S. Pat. No. 5,252,325 to Bires et. al. teaches polyvinylpyrrolidone stabilized silicone shampoos together with a cationic surfactant and ethylene glycol distearate as a suggested pearlescent agent.

Whereas the aforementioned cold pearlescent compositions allegedly provide effective cleaning and luster-producing functionalities, all the formulations continue to use cocodiethanolamide or a derivative and/or sodium laureth sulfate as stabilizing agents for pearlescence or some other related function.

It is an object of the present invention to prepare a novel ultra-mild cold pearlescent concentrate for use in shampoos, skin creams, lipstick, hair colors and the like. More particularly, it is an object of the present invention to prepare a cold pearlescent composition that does not require the presence of the cocodiethanolamide with the potential health problem associated with the nitrosamines possibly formed by its diethanolamine by-product; or the skin irritants, i.e. the sodium lauryl or laureth sulfates. These ingredients are removed altogether from the compositions of the present invention which continue to provide shampoo, lipstick and other skin care products with excellent pearlescent effects and cleansing properties. These pearlescent concentrates also may be prepared without the need for the application of high temperatures often required for blending during the final formulation processes of the prior art.

SUMMARY OF THE INVENTION

The present invention is a novel ultra-mild cold pearlescent concentrate for use in shampoo, lipstick, skin creams, lotions and the like. The pearlizing concentrate is a unique formulation of ingredients comprised of an emulsifier, a zwitterionic surfactant, a nonionic alcohol ethoxylate, and an isethionate or N-methyl taurate which, when processed with other surfactants under conditions well known in the art, impart a brilliant sheen when incorporated into shampoo and soap products.

DETAILED DESCRIPTION OF THE INVENTION

A stable, ultra-mild free flowing cold pearlescent concentrate is prepared using i) a suspending agent emulsifier, preferably a glycol stearate; ii) a zwitterionic surfactant co-emulsifier; iii) a nonionic alcohol ethoxylate; and iv) an isethionate or an N-methyl taurate to obviate the use of cocodiethanolamide and the alkyl sulfates and ethoxylated alkyl sulfates.

The emulsifier comprises from about 15 to about 25 weight percent of the present concentrate, and preferably from about 18 to 22% based on the total weight of the concentrate. The emulsifier is preferably selected from the group consisting of hydroxy stearate, polyethylene glycol mono- and distearates, ethylene glycol mono- and distearates, stearic monoethanolamide, stearic monoethanolamide stearate and mixtures thereof. The most preferred emulsifier is ethylene glycol monostearate ($C_{17}H_{35}COO(CH_2)_2OH$).

A second component of the pearlizing concentrate is a nonionic surfactant. This surfactant, which functions as an emulsion stabilizer in the formulation, is preferably an alcohol ethoxylate, of the formula $$R—O—(CH_2CH_2O)_nH \text{ wherein}$$

R is a $C_8$–$C_{22}$ alkyl, preferably $C_{10}$–$C_{18}$; and n is 1–40, preferably 3–20. The most preferred nonionic is a lauryl alcohol ethoxylate such as Rhodasurf® LA-7, a $C_{12}$ alkyl (7EO) ethoxylated alcohol sold by Rhone-Poulenc Inc.

The nonionic surfactant is incorporated in the cold pearlizing concentrate in an amount of from approximately 1.0 weight percent to about 20.0 weight percent; preferably in an amount of from about 5.0 to about 10.0 weight percent; and most preferably about 7 to 10 weight percent based on the total weight of the concentrate.

In place of the cocodiethanolamides, a zwitterionic surfactant comprises the fourth component of the present invention. Zwitterionic surfactants are those in which the positive and negative groups are equally ionized. Preferably, zwitterionic surfactants known as the betaines and their derivatives are incorporated to provide an enhanced pearlizing effect.

Betaines and amidobetaines are compounds of the general structures:

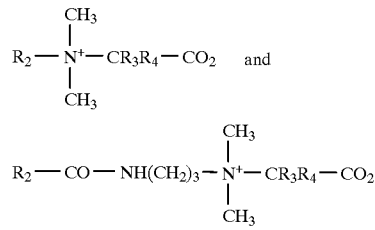

respectively wherein $R_2$ is $C_8$–$C_{22}$ alkyl or alkenyl; $R_3$ is H or $C_1$–$C_4$ alkyl; and $R_4$ is H or $C_1$–$C_4$ alkyl.

The more preferred betaines useful herein include the high alkyl betaines such as cocodimethyl carboxymethyl betaine, lauryl dimethyl carboxymethyl betaine, lauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl) carboxymethyl betaine, oleyl dimethyl gamma-carboxypropyl betaine, and lauryl bis-(2-hydroxypropyl) alpha-carboxyethyl betaine. The sulfobetaines are also preferred and may be represented by cocodimethyl sulfopropyl betaine, stearyldimethyl sulfopropyl betaine, lauryl dimethyl sulfoethyl betaine, and lauryl bis-(2-hydroxyethyl)sulfopropyl betaine. A particularly preferred composition utilizes cocoamidopropyl betaine. The zwitterionic can be present from approximately 1.0 weight percent to about 10 weight percent based on the total weight of the pearlizing concentrate. Preferably, the zwitterionic will comprise from about 2.0 to about 7.0 weight percent of the composition and most preferably from about 3.0 to about 5.0 weight percent of the pearlizing concentrate.

In place of the alkyl and/or alkyl ether sulfates, an isethionate or N-methyl taurate is utilized in the concentrates of this invention.

The isethionates are of the formula:

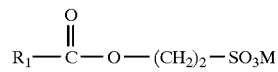

wherein $R_1$ is a fatty alkyl group and M is a counterion selected from the group consisting of sodium, calcium, magnesium, ammonium and triethanolamine, some of which are commercially available as the Geropon® AS series (Rhone-Poulenc Inc.). The preferred isethionate is sodium cocoyl isethionate.

The N-methyl taurates are of the formula:

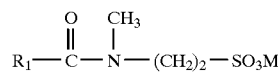

wherein $R_1$ and M are as described above, some of which are commercially available as the Geropon® T series (Rhone- Poulenc Inc.). The preferred N-methyl taurate is sodium cocoyl N-methyl taurate.

The isethionates and/or taurates of this invention may be incorporated into the pearlizing concentrates at from about 5.0 to about 25 weight percent, preferably about 8 to about 20 weight percent based on the total weight of the concentrate.

It was surprisingly discovered that the above isethionates and taurates provide excellent dispersing and stabilizing properties to the ultra-mild, cold pearlizing concentrates.

Water, preferably deionized, is then added in an amount from about 20 weight percent to about 78 weight percent, preferably from about 41 to about 67 weight percent based on the total weight of the concentrate.

The formulated shampoo and soap systems utilizing the cold pearlizing concentrate of the present invention can contain a variety of non-essential optional components suitable for rendering such compositions more acceptable. Such conventional optional ingredients are well known to those skilled in the art, e.g., preservatives such as benzyl alcohol, methyl paraben, propyl paraben and imidazolidinyl urea; cationic surfactants such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; thickeners and viscosity modifiers such as block polymers of ethylene oxide and propylene oxide, e.g. Antarox F-88 (Rhone-Poulenc Inc.), sodium chloride, sodium sulfate, polyvinyl alcohol, and ethyl alcohol; pH adjusting agents such as citric acid, succinic acid, phosphoric acid, sodium hydroxide, sodium carbonate; perfumes; dyes; and sequestering agents such as disodium ethylenediamine tetra-acetate. Such agents generally are used individually at levels of from about 0.01% to about 10%, preferably from 0.5% to about 5.0% by weight of the composition.

The pH of the present compositions is not critical and may be in the range of from about 5 to about 9. The pH can be adjusted using a buffer such as citric acid.

The order of addition to the mixing tank of the individual components of the concentrate is not critical nor is the reasonably elevated temperature; however, preferably the water, emulsifier and isethionate or N-methyl taurate surfactant are intimately blended at from about 60° to 80° C., more preferably from about 70° to 75° C. with high agitation until the emulsifier is solubilized. The nonionic surfactant and zwitterionic are then blended into the mix. The concentrate is then stored at a temperature of from about 35° C. to about 60° C., preferably from about 45° C. to about 55° C. for at least one day and preferably two (2) days in order to fully develop its pearlescent characteristics.

The shampoos and soaps of the present invention can be made by merely mixing the materials together with the concentrate at room temperature.

The ultra-mild cold pearlizing concentrate of the present invention may be specifically formulated into a number of different blended soap products. The pearlizing concentrate not only imparts a high luster pearlescence and sheen to the products, but also contributes emollient and moisturizing qualities to the skin. It provides superior shampoo, bath and shower soap systems and markedly improves wet comb-out of the hair.

The following examples are provided to better describe and define the compositions of the present invention. They are for illustrative purposes only, and it is realized that minor changes and variations may be made with respect to these compositions that are not shown below. Such changes that do not materially alter the compositions formulation or function are still considered to fall within the spirit and scope of the invention as recited by the claims that follow.

EXAMPLE I

The following components and their respective amounts in a weight percent of the total basis are assembled.

| Formulation A | |
|---|---|
| Ethylene glycol monostearate (EGMS) | 20.0 |
| Laureth(7EO) alcohol | 8.0 |
| Sodium cocyl N-methyl taurate | 15.0 |
| Cocoamidopropyl betaine | 3.0 |
| Deionized water | 54.0 |
| Formulation B | |
| Ethylene glycol monostearate | 25.0 |
| Laureth(7EO) alcohol | 8.0 |
| Sodium cocyl N-methyl taurate | 17.0 |
| Cocoamidopropyl betaine | 3.0 |
| Deionized water | 47.0 |
| Formulation C | |
| Ethylene glycol monostearate | 15.0 |
| Laureth(7EO) alcohol | 8.0 |
| Sodium cocyl N-methyl taurate | 10.0 |
| Cocoamidopropyl betaine | 5.0 |
| Deionized water | 62.0 |

In all three formulations, in order to prepare the ultra-mild cold pearlizing concentrates of the present invention, the ethylene glycol monostearate is mixed with water and the sodium cocoyl N-methyl taurate or the sodium cocoyl isethionate at 70° to 75° C. with high speed agitation. After the EGMS is completely solubilized, the lauryl (7EO) alcohol and the cocoamidopropyl betaine are added into the mixture with stirring and kept at 50° C. for one to two days in order to develop the pearlescence fully. The maintenance of the emulsion at this temperature for this period of time is important for the full development of the pearlescence.

The pearlescence concentrate produced is an iridescent or shiny white to off-white viscous liquid with a pH of from about 6.5–7.5 and realizes excellent dispersibility in water.

As is true with all of the compositions of this invention, these unique performance stabilizing and pearlizing concentrates require no heating for blending and are readily compatible with most anionic-based liquid hand cleaner, shampoo, bubble bath and cosmetic systems to form attractive high-performance very mild products.

EXAMPLE II

The following ingredients and their respective amounts are combined to produce a pearlescent liquid hand soap. The amounts given are weight percent based on the total weight.

| | |
|---|---|
| RHODACAL° A-246/L* | 23.4 |
| Forumlation A Concentrate | 12.0 |
| Citric Acid (to pH 6.5–7.0) | Q.S. |
| Perfume, Dye, Preservative | Q.S. |
| Sodium Chloride | 4.0 |
| Water, Deionized | 60.6 |

*Sodium alpha olefin sulfonate (40% active - Rhone-Poulenc Inc.)

The water is charged into a mixing vessel and the active ingredients are slowly mixed at room temperature until the mixture becomes uniform in appearance and texture. Citric acid (50%) is then added in an amount sufficient to adjust the pH to 6.0. The shampoo is then fragranced with a suitable perfume as desired and colored with an appropriate FD & C dye. The hand soap provides excellent lather and cleaning, is extremely mild, and leaves the hands soft.

EXAMPLE III

The following ingredients and their respective amounts are combined to produce an ultra-mild pearlescent body shampoo. The amounts given are in weight percent based on the total weight.

| | |
|---|---|
| RHODAPON SB-8208/S | 17.2 |
| GEROPON SBFA 30 (i) | 4.2 |
| MIRATAINE BET C-30 (ii) | 7.7 |
| Formulation B Concentrate | 8.5 |
| Perfume, Dye, Preservative | Q.S. |
| Water | 62.4 |

(i) disodium laureth (3EO) sulfo succinate (30% active - Rhone-Poulenc Inc.)
(ii) cocoamido propyl betaine (30% active - Rhone-Poulenc Inc.)

The ingredients are easily blended as in Example II. These pearlescent specialty bath and shower formulations contribute to a luxurious, smooth feel and they help to keep the skin soft and supple.

EXAMPLE IV

A body shampoo is prepared as in Example III with the use of Formulation C concentrate in lieu of Formulation B. As in Example II, the pearlescent liquid products are prepared easily at room temperature and the Formulation C concentrate provides enhanced viscosity building, foam stability and lather enrichment properties; all combined in an extremely mild formulation.

What we claim is:

1. An ultra-mild, cold pearlizing concentrate comprising:
 a) from about 15 to 25 percent by weight of an emulsifier selected from the group consisting of hydroxy stearate, polyethylene glycol monostearate, polyethylene glycol distearate, ethylene glycol monostearate, ethylene glycol distearate, stearic monoethanolamide, stearic monoethanolamide stearate, and mixtures thereof;
 b) a nonionic alcohol ethoxylate of the formula:

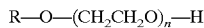

wherein R is a $C_8$ to $C_{22}$ alkyl and n is 1 to 40;
 c) from about 5 to 25 weight percent of a surfactant selected from the group consisting of isethionates wherein
  i) the isethionates are of the formula:

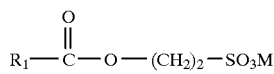

wherein $R_1$ is a fatty $C_2$ to $C_{14}$ alkyl group and M is a counterion selected from the group consisting of sodium, calcium, magnesium, ammonium and triethanolamine; and
 d) a zwitterionic surfactant selected from the group consisting of
  i) betaines
  ii) amidobetaines, and
  iii) sulfobetaines; and
 e) water.

2. The ultra-mild, cold pearlizing concentrate of claim 1 wherein the zwitterionic surfactant is selected from the group consisting of cocodimethyl carboxymethyl betaine, lauryl dimethyl carboxymethyl betaine, lauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, lauryl bis-(2-hydroxypropyl)alpha-carboxyethyl betaine, cocodimethyl sulfopropyl betaine, stearyldimethyl sulfopropyl betaine, lauryldimethyl sulfoethyl betaine, lauryl bis-(2-hydroxy-ethyl)sulfopropyl betaine, and cocoamidopropyl betaine.

3. The ultra-mild, cold pearlizing concentrate of claim 2 wherein
 a) the emulsifier is ethylene glycol monostearate;
 b) the nonionic alcohol ethoxylate is lauryl (7EO) alcohol;
 c) the isethionate surfactant is sodium cocoyl isethionate; and
 d) the zwitterionic surfactant is cocoamidopropyl betaine.

4. The ultra-mild, cold pearlizing concentrate of claim 2 wherein
 a) the emulsifier is present from about 15 to 25 percent by weight;
 b) the nonionic alcohol ethoxylate is present from about 1 to about 20 weight percent;
 c) the isethionate surfactant is present from about 5 to about 25 weight percent; and
 d) the zwitterionic surfactant is present from about 1 to about 10 weight percent;
all of the weight percents being based on the total weight of the pearlizing concentrate.

5. The ultra-mild, cold pearlizing concentrate of claim 4 wherein
 a) the emulsifier is present from about 18 to about 22 weight percent;
 b) the nonionic alcohol ethoxylate is present from about 5 to about 10 weight percent;
 c) the isethionate surfactant is present from about 8 to about 20 weight percent; and
 d) the zwitterionic surfactant is present from about 2 to about 7 weight percent;
all of the weight percents being based on the total weight of the pearlizing concentrate.

6. An ultra-mild shampoo composition comprising the cold pearlizing concentrate of claim 1.

7. An ultra-mild hand and body soap composition comprising the cold pearlizing concentrate of claim 1.

8. An ultra-mild bubble bath composition comprising the cold pearlizing concentrate of claim 1.

9. A method for preparing an ultra-mild pearlizing concentrate comprising:
 intimately blending the ingredients of claim 2 at from about 60° C. to about 80° C. until the emulsifier is solubilized.

* * * * *